(12) United States Patent
Täubert et al.

(10) Patent No.: US 7,806,836 B2
(45) Date of Patent: Oct. 5, 2010

(54) GUIDE WIRE AND IMPLANTABLE ELECTRODE LINE

(75) Inventors: Kerstin Täubert, Berlin (DE); Siegfried Voigt, Berlin (DE); Erhard Flach, Berlin (DE); Gernot Kolberg, Berlin (DE); Gerhard Hahnke, Berlin (DE); Agur Junge, Berlin (DE)

(73) Assignee: Biotronik Meβ-und Therapiergeräte GmbH & Co. (DE)

( * ) Notice: Subject to any disclaimer, the term of this patent is extended or adjusted under 35 U.S.C. 154(b) by 1051 days.

(21) Appl. No.: 10/364,998

(22) Filed: Feb. 12, 2003

(65) Prior Publication Data

US 2003/0153966 A1    Aug. 14, 2003

(30) Foreign Application Priority Data

Feb. 12, 2002    (DE) ................. 102 05 721

(51) Int. Cl.
*A61B 5/04* (2006.01)
*A61M 25/00* (2006.01)
(52) U.S. Cl. ...................... 600/585; 600/373
(58) Field of Classification Search ........... 600/585, 600/433, 434, 435, 373; 607/122; 606/129
See application file for complete search history.

(56) References Cited

U.S. PATENT DOCUMENTS

| | | | |
|---|---|---|---|
| 4,570,642 A | | 2/1986 | Kane et al. |
| 4,886,065 A | * | 12/1989 | Collins, Jr. .................. 600/377 |
| 4,954,105 A | * | 9/1990 | Fischer ....................... 439/864 |
| 5,228,455 A | | 7/1993 | Barcel |
| 5,364,340 A | * | 11/1994 | Coll ............................... 604/8 |
| 5,374,252 A | * | 12/1994 | Banks et al. ................ 604/158 |
| 5,456,708 A | * | 10/1995 | Doan et al. .................. 607/127 |
| 5,497,782 A | | 3/1996 | Fugoso |
| 5,738,683 A | | 4/1998 | Osypka |
| 5,871,531 A | * | 2/1999 | Struble ........................ 607/126 |
| 6,033,414 A | * | 3/2000 | Tockman et al. ............. 606/129 |
| 6,039,722 A | * | 3/2000 | Greive ......................... 604/528 |
| 6,050,034 A | * | 4/2000 | Krinner ........................ 52/155 |

(Continued)

FOREIGN PATENT DOCUMENTS

DE    4425195 C1    11/1995

(Continued)

OTHER PUBLICATIONS

Federal Republic of Germany International Search Report, Appl. No. 102 05 721.4 (3 pgs.).

(Continued)

*Primary Examiner*—Max Hindenburg
*Assistant Examiner*—Jonathan M Foreman
(74) *Attorney, Agent, or Firm*—Armstrong Teasdale LLP

(57) ABSTRACT

A guide wire for introducing an implantable electrode line, wherein the electrode line is particular a heart electrode line for intracardial sensing of cardiac actionpotentials and/or for electrical stimulation or defibrillation of the heart, and wherein the guide wire is adapted for interlocking with the electrode line, and wherein the guide wire comprises a deformation, in particular curved, wavy, V-shaped, zig-zag, or trapezoidal, enlarging the effective contact diameter of the guide wire to a value corresponding essentially to the inner diameter of a lumen of the electrode line or greater than this.

4 Claims, 3 Drawing Sheets

U.S. PATENT DOCUMENTS

| | | | |
|---|---|---|---|
| 6,059,484 A * | 5/2000 | Greive ........................ 403/305 |
| 6,203,561 B1 * | 3/2001 | Ramee et al. ................ 606/200 |
| 6,254,610 B1 * | 7/2001 | Darvish et al. .............. 606/108 |
| 6,406,442 B1 * | 6/2002 | McFann et al. ............. 600/585 |
| 6,456,890 B2 | 9/2002 | Pianca et al. |
| 6,512,959 B1 * | 1/2003 | Gomperz et al. ............ 607/122 |
| 6,714,809 B2 * | 3/2004 | Lee et al. ..................... 600/423 |
| 6,882,886 B1 | 4/2005 | Witte et al. |
| 2001/0000349 A1 | 4/2001 | Coe et al. |

FOREIGN PATENT DOCUMENTS

DE  19838360 A1  10/1999

OTHER PUBLICATIONS

European Search Report (4 pgs.); In re Appl. no. M/BTR-016-EP.

* cited by examiner

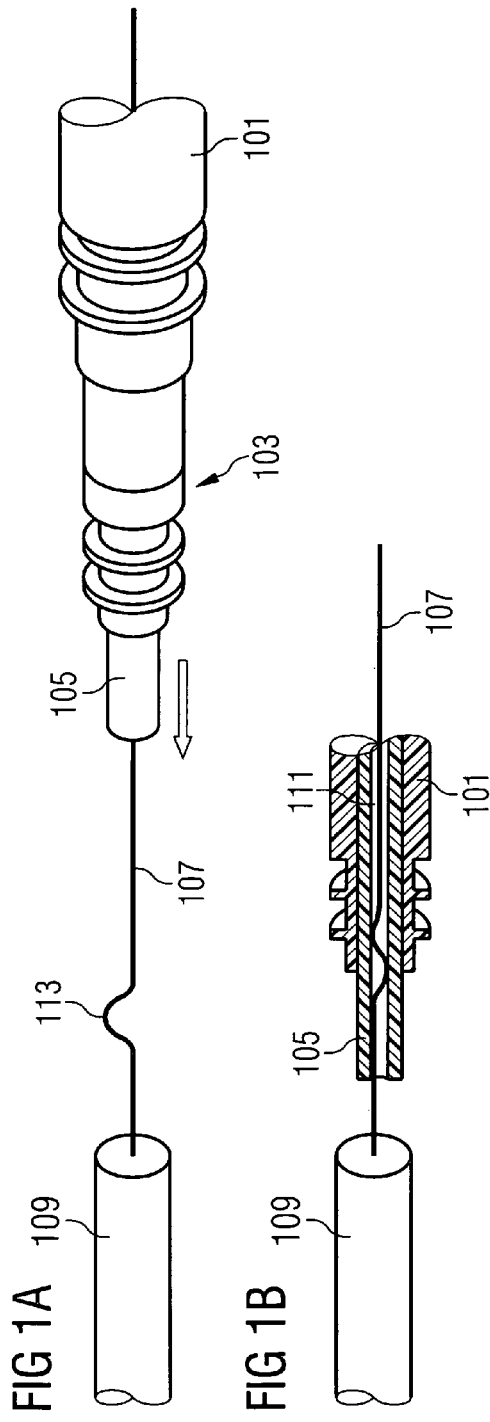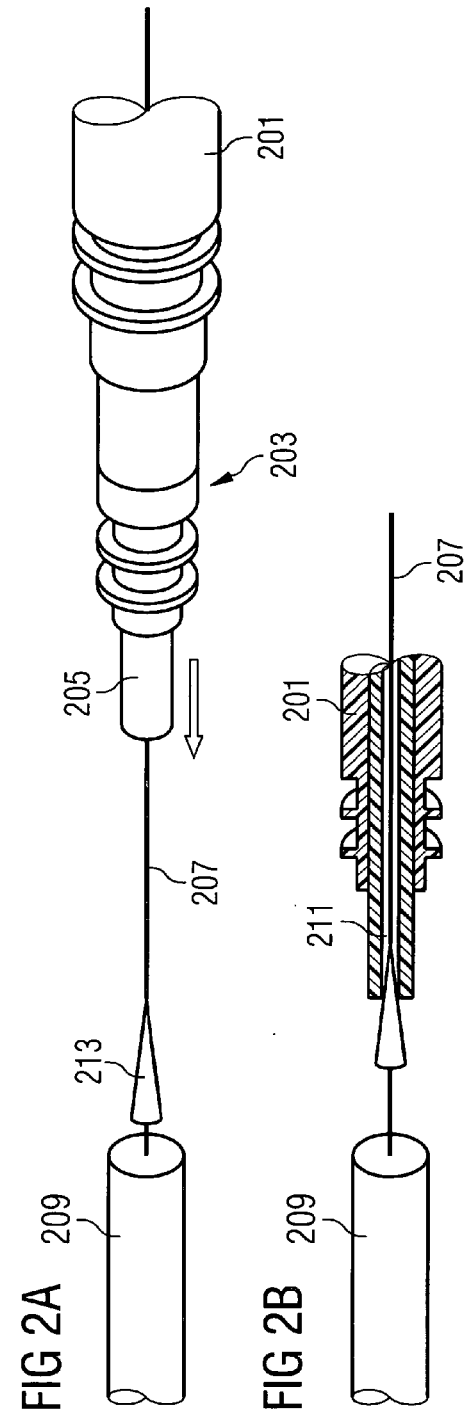

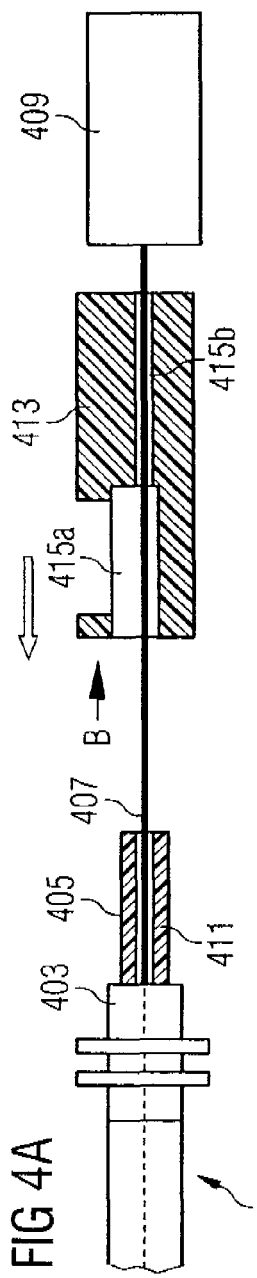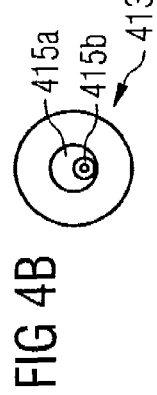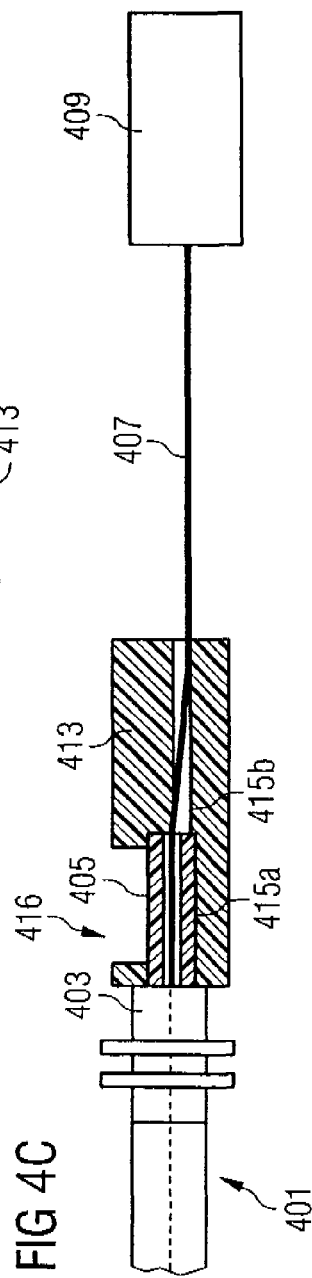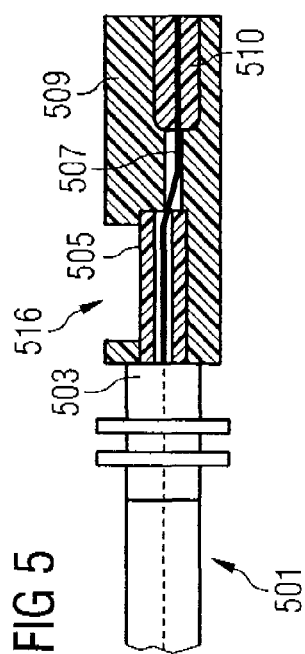

GUIDE WIRE AND IMPLANTABLE ELECTRODE LINE

CROSS REFERENCE TO RELATED APPLICATIONS

This application claims the benefit of German Patent Application No. 102 05 721.4 filed Feb. 12, 2002, which is hereby incorporated by reference in its entirety.

BACKGROUND OF THE INVENTION

The invention relates to a guide wire for introducing an implantable electrode line, in particular a heart electrode line for intracardial sensing of cardiac action potentials and/or for electrical stimulation or defibrillation of the heart as well as a corresponding electrode line itself, and finally a combination of a guide wire and an electrode line.

Implantable electrode lines with said functions have been known for a long time and in a great variety of forms in connection with implantable pacemakers or defibrillators heavily used in practice. Since these electrode lines, due to the course of the vascular system in which they extend from the implantable device into the heart of the patient, must have a high degree of flexibility, a guide wire is needed as a tool for their implantation. In order to be able to receive the guide wire, the electrode lines have a cavity extending in the longitudinal direction, the so-called lumen. With the guide wire used, the electrode line can be guided, with observation of its path by means of an imaging process, with precise targeting into heart, where, if needed, it is possible, by turning a grip on the proximal end of the guide wire, to steer its distal end, provided with a curvature, in the desired direction.

In the case of the known implantation processes of this type the guide wire (mandrin) is pushed in up to the distal stop in the electrode line. Thereby the electrode is, if necessary, stretched and obtains a curve and rigidity, which make possible its introduction into the heart through the (venous) vascular system—which however assumes that the guide wire remains in place reliably, essentially over the entire extension of the lumen of the electrode line. As a consequence of the diverse manipulations by the implanter however, unintended displacements occur relatively frequently in the customary arrangements and under certain circumstances the guide wire slips out of the lumen of the electrode line.

From U.S. Pat. No. 5,497,782 a lockable guide wire for inserting and replacing a dilatation catheter is known. There a spirally expandable section of the guide wire serves for its reliable positioning relative to a lesion when the dilatation catheter pulled out and replaced by a new one.

From U.S. Pat. No. 6,027,461 an infusion guide wire with fixed core wire is known. The proximal end of this core wire is affixed to a proximal connecting housing for the connection of an infusion lumen.

BRIEF DESCRIPTION OF THE INVENTION

The objective of the invention consists of specifying an improved guide wire for an implantable electrode line or a corresponding electrode line per se, which insures a reliable and rapid implantation even under adverse circumstances, for example, in the case of a very unfavorable geometric course of the vascular systems and the corresponding necessity of complicated handling on the part of the implanter.

The invention comprises the fundamental concept of providing a mutual interlocking between the guide wire and electrode line for fastening the mandrin in the lumen of the electrode line during the implantation process. It further comprises the concept of providing a fastening or interlocking of this type on or near the proximal end of the electrode-mandrin arrangement in order, after finishing the implantation, to be able to detach it once again as easily as possible. It is to be noted in this, that the proposed fixation does not necessarily assume that the guide wire has been pushed in completely up to the distal end of the electrode line lumen.

A first expedient form of embodiment provides a deformation, in particular curved, wavy, V-shaped, zig-zag, or trapezoidal, enlarging the effective contact diameter of the guide wire to a value corresponding essentially to the inner diameter of a lumen of the electrode line or greater than this. The high degree of elasticity of the material of the guide wire, in conjunction with this impressed deformation, leads to the guide wire being pressed pointwise (at one point or several points) elastically against the wall of the lumen, whereby a frictional lock with the electrode line, and thus the desired locking, is realized. Said deformation represents a particularly simple fixation means.

In an alternative embodiment the fixation means is a thickening, formed on or fixedly applied, which has an engagement section tapering toward the distal end of the guide wire, in particular in the form of the frustum of a cone, for forcelocking engagement with a lumen of the electrode line. Said thickening can be a thin cone, but also an element with one or more curved surfaces, and it can, for example, consist of metal or also of plastic and be welded or glued to the actual guide wire.

An additional alternative embodiment provides a first catching means, formed on or fixedly applied, which is formed to work together with correspondingly formed and disposed second catching means on the electrode line. Catching means of this type are known per se and need no further description here.

An additional, from the present view preferred, embodiment comprises an attached or mounted split taper socket, which is formed to engage a plug pin of the electrode line and to produce a force-locking engagement with it. In this case the split taper socket can consist of elastic material in such a manner that it can be pushed on the plug pin and encloses it elastically after being pushed on.

In a somewhat modified embodiment the interlocking element is a an attached or mounted split taper socket which is formed to produce a coupling in the longitudinal direction of the guide wire in its area lying in a lumen of the electrode line, and thus a force-locking engagement between the guide wire and the electrode line. This split taper socket can, on the one hand, be displaceably mounted on the guide wire or, on the other hand however, be an attached or mounted split taper socket. It is formed to produce a coupling in the longitudinal direction of the guide wire in its area lying in a lumen of the electrode line, and thus a force-locking engagement between the guide wire and the electrode line.

For the realization of said coupling it has in particular two longitudinal holes adjacent to one another in the longitudinal direction but not concentric to one another where the diameter of the first, proximal longitudinal hole is matched to the outer diameter of the guide wire and the diameter of the second, distal longitudinal hole is matched to the outer diameter of a plug pin of the electrode line.

The electrode line proposed in addition for the realization of the existing objective has, in preferred embodiments, fixation means which correspond in principle to the above-mentioned fixation means on the guide wire.

In a first embodiment such an electrode line has an elastic stopper, inserted in a lumen of the electrode line, with a central hole, which is dimensioned in such a manner that it effects force-locking engagement with the electrode wire at a predefined retaining force. Said stopper is, in a particularly simple manner, inserted at the proximal end of the electrode line in a plug pin located there. In a somewhat modified embodiment it has a longitudinal hole disposed eccentrically and/or inclined to the longitudinal axis, said longitudinal hole, on insertion of the guide wire, effecting a coupling in the longitudinal extension of the same in the lumen, and thus a force-locking engagement between the guide wire and the electrode line. This latter embodiment therefore acts similarly to an embodiment of the aforementioned split taper socket on the guide wire.

BRIEF DESCRIPTION OF THE DRAWINGS

Advantages and expediencies of the invention in other regards follow from the subordinate claims as well as the following, schematic description of preferred embodiment examples with the aid of the figures. Shown by these are:

FIGS. 1A and 1B schematic perspective representations of a first form of embodiment of a guide wire according to the invention, FIGS. 2A and 2B schematic perspective representations of a second form of embodiment of a guide wire according to the invention, FIGS. 3A and 3B schematic perspective representations of a third form of embodiment of a guide wire according to the invention, FIGS. 4A to 4C schematic representations (longitudinal sectional representations or frontal view of the split taper socket) of a fourth form of embodiment of a guide wire according to the invention, and FIG. 5 schematic longitudinal sectional representation of a modification of the fourth form of embodiment.

DETAILED DESCRIPTION OF THE INVENTION

Figure 3A:
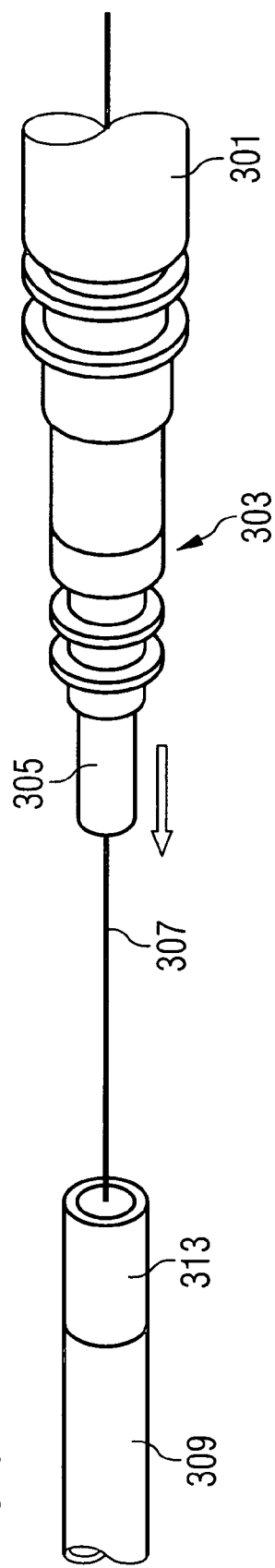

FIGS. 1A and 1B show, in schematic perspective representations (in FIG. 1B partially sectioned), the proximal end of an implantable electrode line 101 with a multipole plug 103, which includes a plug pin 105, with an introduced guide wire 107 with grip piece 109. In FIG. 1B it is to be seen that the electrode line 101—including the plug 103—has a central lumen 111, through which the guide wire 107 goes.

Near to the proximal end of the guide wire 107, shortly before it joins the grip piece 109, the guide wire has a curved deformation 113 whose effective diameter increases to a value greater than the inner diameter of the lumen 111. As FIG. 1B shows, on pushing the guide wire into the lumen 111 up to a point beyond the position of the deformation 113 a wavy elastic deformation of the corresponding section of the guide wire takes place. This leads to an elastic contact pressure of the guide wire at several points of the inner wall of the lumen 111, whereby a frictional lock between the guide wire 107 and the electrode line 101 is produced.

With structuring of the deformation 113 which is appropriate and matched to the elasticity properties of the guide wire and the coefficient of frictional drag between the guide wire and the wall of the lumen, the frictional force is sufficient to hold the guide wire securely in the electrode line during all the manipulations occurring in connection with introduction of the electrode line into the heart of a patient. After finishing the implantation, the guide wire 107 can once again be pulled, at the grip piece 109, out of the electrode line with the electrode line 101 fixed in the area of the plug 103 when this frictional force is surmounted.

In FIGS. 2A and 2B an additional arrangement of an electrode line 201 with a plug 203 as well as a corresponding plug pin 205 and a guide wire 207 with grip piece 209, is represented. Here, for fixation of the guide wire in a lumen 211 of the electrode line 201, a wedge-like cap 213 is provided on the guide wire 207 in the immediate vicinity of the distal apical face of the grip piece 209. As is to be seen in FIG. 2, on introduction of the guide wire into the lumen of the electrode line, the wedge 213—which preferably consists of a material with a high coefficient of friction with respect to the material of the wall of the lumen 211—is partially pushed into the lumen. In so doing it is pressed against the outermost proximal section of the lumen wall, and a frictional lock also arises here, which (assuming suitable choice of material and dimensioning) holds the guide wire 207 securely in the electrode line 201 during any manipulation.

Figure 3B:
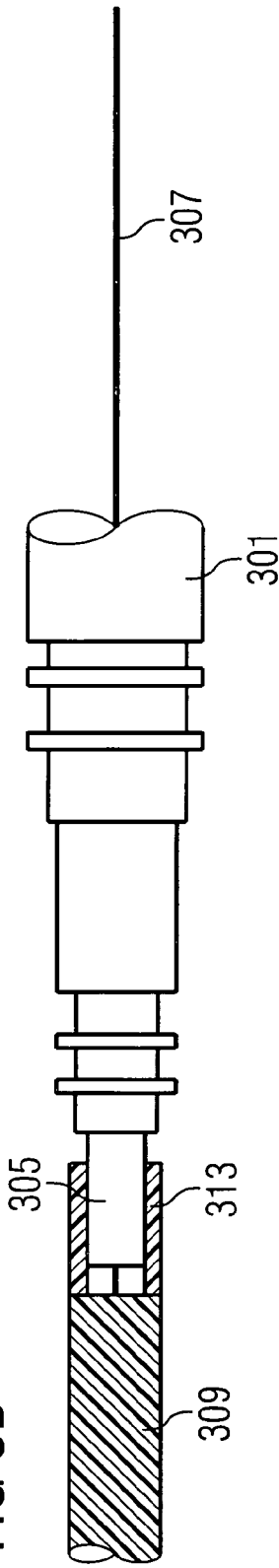

As an additional form of embodiment, an additional arrangement of an electrode line 301 with plug area 303 and plug pin 305 and a guide wire 207 with grip piece 309 is represented in FIGS. 3A and 3B—once again schematically. Here an annular elastomer extension 313 at the distal end of the grip piece 309 is provided as an interlocking element, acting via a force-lock, between the electrode line and guide wire.

As is illustrated in FIG. 3B, the elastomer extension (for example, rubber ring) 313 surrounds the circumference of the plug pin 305 and exerts on it an elastic contact force. It can be adjusted again by suitable choice of material and dimensioning of both parts in such a manner that the guide wire is held securely in the electrode line for the duration of the implantation process and nevertheless is relatively easy to remove from it once again after the introduction is finished. Instead of an elastomer a relatively hard thermoplastic part can also be used here.

In FIGS. 4A to 4C an additional embodiment is represented schematically, in which an electrode line 401 with plug area 403 and plug pin 405 is plugged onto a guide wire 407 which has a grip piece 409. Here, as a locking element between the electrode line 401 and the guide wire 407, a separate split taper socket 413 is provided which can be displaced on the guide wire, said split taper socket having two longitudinal holes 415a, 415b adjacent to one another in the longitudinal direction with different diameters and disposed eccentrically to one another.

As FIG. 4C shows schematically in the state of the guide wire 407 introduced into a lumen 411 of the electrode line 401, on pushing the distal longitudinal hole 415a of the split taper socket 413 onto the plug pin 405, a coupling of the guide wire in its longitudinal extension is effected. This leads to a pressing of the same against the wall of the hole 415b near its distal and proximal end. Since at the same time the split taper socket 413 is formed, with regard to its dimensions and choice of material, in such a way that the plug pin 405 is also fixed in the hole 415a by a frictional lock, fixation between the guide wire and electrode line results overall. This prevents the former from slipping out of the latter as a consequence of manipulations during the implantation process. In the area of the distal hole 415a the split taper socket 413 has a connection window 416, via which, if required, the plug pin 405 can be contacted electrically from outside.

If during the implantation of the electrode line 401 the correct position for the guide wire found, the split taper socket 413 is pushed onto the plug 403, where the plug pin 405 penetrates into the distal hole 415a of the split taper socket. In so doing, due to the axial offset of the holes 415a, 415b in the split taper socket, said coupling or oblique position of the guide wire 407 is produced, which leads to locking between the guide wire and electrode line. The electrode line can then be pushed further forward without the guide wire being able to change its position relative to it. After the implantation is finished, the split taper socket 413 is pulled out of the electrode plug 403 once again and then the guide wire 407 can also be pulled, at the grip piece 409, out of the electrode line once again without further effort.

In FIG. 5 a modified realization of the latter functional principle with an electrode line 501 (with plug 503 and plug pin 505, consistent with the embodiment according to FIGS. 4A to 4C) and a guide wire 507 with a grip piece 509 acting at same time as split taper socket is represented. The grip piece 509 has a design substantially consistent with the design of the split taper socket 413 according to FIGS. 4A to 4C, where the guide wire is held in a fixation stopper 510, which is integrated in the proximal end of the grip piece. A connection window (denoted by 516) is also provided here.

The embodiment of the invention is not restricted to the examples described above, but rather is just as well possible in a plurality of modifications, which lie within the scope of practice according to the art.

What is claimed is:

1. A system for introducing an implantable electrode line, said system comprising:
   an electrode line comprising a plug pin including an inner surface defining a channel;
   a guide wire configured to interlock with the electrode line, wherein the channel receives the guide wire therethrough such that the inner surface of the plug pin is substantially parallel to the guide wire; and
   a socket configured to generate deformation of the guide wire to produce a coupling in a longitudinal direction of the guide wire within a lumen of the electrode line, the coupling forming a force-locking engagement between the guide wire and the electrode line, wherein the socket is configured to receive the plug pin in a friction fit configuration and is movable with respect to the electrode line in the longitudinal direction of the guide wire to generate the deformation and the force-locking engagement,
   the socket comprising two longitudinal passages that are adjacent to one another in the longitudinal direction but not concentric to one another, wherein a diameter of a first, proximal longitudinal passage is matched to an outer diameter of the guide wire and a diameter of a second, distal longitudinal passage is matched to an outer diameter of the plug pin.

2. A system according to claim 1, wherein the socket is displaceably mounted to the guide wire.

3. A system according to claim 1, wherein the socket comprises an elastic material such that the socket can be pushed on the plug pin to enclose the plug pin elastically.

4. A system according to claim 1, wherein the socket comprises a first end and an opposing second end, the socket defining a first passage that extends from the first end along a first axis and a second passage in communication with the first passage that extends from the second end along a second axis different than the first axis, and a plug operatively coupled to the electrode line and at least partially positioned within the first passage such that the guide wire extends through the socket from the first end to the second end.

* * * * *